US009914126B2

(12) United States Patent
Chan

(10) Patent No.: US 9,914,126 B2
(45) Date of Patent: Mar. 13, 2018

(54) STORAGE CONTAINER FOR BIOSENSOR TEST ELEMENTS

(75) Inventor: Frank A. Chan, Sunnyvale, CA (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1287 days.

(21) Appl. No.: 13/305,005

(22) Filed: Nov. 28, 2011

(65) Prior Publication Data
US 2013/0134159 A1    May 30, 2013

(51) Int. Cl.
*B65D 25/10* (2006.01)
*B65D 25/02* (2006.01)
(Continued)

(52) U.S. Cl.
CPC .............. *B01L 9/52* (2013.01); *B01L 3/508* (2013.01); *B01L 99/00* (2013.01);
(Continued)

(58) Field of Classification Search
CPC ....... G01N 33/48757; G01N 33/48778; G01N 33/4875; A61B 50/30; A61B 10/0096; B65D 25/107; B65D 25/10; B65D 25/101; B65D 25/04; B65D 81/266; B65D 2543/00083
USPC .... 220/837, 501, 528, 23.89, 656, 657, 659, 220/628, 629, 630, 636, 23.87; 206/569, 206/305, 449, 204; 422/555, 68.1, 547, 422/560, 554, 563, 549–550, 565;
(Continued)

(56) References Cited

U.S. PATENT DOCUMENTS 375,412 A * 12/1887 Creque .................. 248/159
1,450,674 A * 4/1923 Marston .................. 220/8
(Continued)

FOREIGN PATENT DOCUMENTS

WO    WO 2009/030616    3/2009
WO    WO 2009/140627    11/2009

OTHER PUBLICATIONS

International Search Report; PCT/EP2012/004846; dated Mar. 8, 2013; 5 pages.
(Continued)

*Primary Examiner* — J. Gregory Pickett
*Assistant Examiner* — Gideon Weinerth
(74) *Attorney, Agent, or Firm* — Woodard, Emhardt, Moriarty, McNett & Henry, LLP

(57) ABSTRACT

A component for a storage container configured to receive vertically oriented articles. The component includes a tubular sidewall extending longitudinally from a base, and at least one spacer portion extending from an underside of the base and configured for engagement with an interior surface of a corresponding storage container. The component also includes at least one pair of retainer elements extending laterally from an inner surface of the tubular sidewall and inwardly into an interior region of the component, and with the retainer elements being oppositely oriented and configured to retain a vertically oriented article therebetween by frictional engagement with opposite longitudinal edges of the article, and wherein an insertion force for resilient deflection of the retainer elements during insertion of the article is less than a removal force for resilient deflection of the retainer elements during removal of the article.

9 Claims, 6 Drawing Sheets

(51) Int. Cl.
  *B01L 9/00* (2006.01)
  *B01L 3/00* (2006.01)
  *B01L 99/00* (2010.01)
  *G01N 33/487* (2006.01)

(52) U.S. Cl.
  CPC .. *G01N 33/48778* (2013.01); *B01L 2200/022* (2013.01); *B01L 2200/025* (2013.01); *B01L 2200/028* (2013.01); *B01L 2300/043* (2013.01); *B01L 2300/0609* (2013.01); *B01L 2300/0825* (2013.01); *B01L 2300/0832* (2013.01); *B01L 2300/0851* (2013.01); *B01L 2300/0858* (2013.01)

(58) Field of Classification Search
  USPC ........ 211/207; 248/670, 449, 132, 161, 157, 248/419
  See application file for complete search history.

(56) References Cited

U.S. PATENT DOCUMENTS

| | | | | |
|---|---|---|---|---|
| 2,487,107 A * | 11/1949 | Andrea | ............... | B65D 25/38 206/804 |
| 2,727,547 A * | 12/1955 | Moon | ............... | 220/555 |
| 3,096,960 A * | 7/1963 | Kinney | ............... | 248/113 |
| 3,918,920 A * | 11/1975 | Barber | ............... | 422/560 |
| 4,911,344 A | 3/1990 | Kahler | | |
| 5,080,232 A * | 1/1992 | Leoncavallo et al. | ........ | 206/446 |
| 5,275,367 A * | 1/1994 | Frye | ............... | 248/205.3 |
| 5,316,146 A * | 5/1994 | Graff | ............... | 206/438 |
| 5,505,308 A * | 4/1996 | Eikmeier et al. | ............. | 206/449 |
| 5,788,064 A | 8/1998 | Sacherer et al. | | |
| 5,967,318 A * | 10/1999 | Rosler | ............... | 206/372 |
| 6,502,711 B1 * | 1/2003 | McRae | ............... | 220/23.4 |
| 6,872,358 B2 | 3/2005 | Hagen et al. | | |
| 6,908,008 B2 | 6/2005 | Pugh | | |
| 7,059,492 B2 | 6/2006 | Giraud et al. | | |
| 7,063,234 B2 | 6/2006 | Giraud | | |
| 7,172,728 B2 | 2/2007 | Otake | | |
| 7,501,093 B2 | 3/2009 | Demelo et al. | | |
| 7,552,843 B2 | 6/2009 | Kuriger et al. | | |
| D599,032 S | 8/2009 | Bucholtz et al. | | |
| D599,322 S | 8/2009 | Bucholtz et al. | | |
| 7,582,262 B2 | 9/2009 | Funke et al. | | |
| D631,168 S | 1/2011 | Bucholtz et al. | | |
| 8,394,343 B2 * | 3/2013 | Chan et al. | ............... | 422/555 |
| 2004/0007585 A1 | 1/2004 | Griffith et al. | | |
| 2004/0209755 A1 * | 10/2004 | Moore et al. | ............... | 494/20 |
| 2005/0218024 A1 * | 10/2005 | Lang et al. | ............... | 206/438 |
| 2007/0034630 A1 | 2/2007 | Lancesseur et al. | | |
| 2007/0108076 A1 * | 5/2007 | Miller et al. | ............... | 206/373 |
| 2010/0140116 A1 | 6/2010 | Stiene et al. | | |
| 2011/0056951 A1 * | 3/2011 | Wooldridge | ............. | 220/495.01 |
| 2011/0127175 A1 | 6/2011 | Chan et al. | | |
| 2011/0127269 A1 | 6/2011 | Bucholtz et al. | | |
| 2011/0174644 A1 * | 7/2011 | Chan et al. | ............... | 206/305 |
| 2011/0210021 A1 | 9/2011 | Logel et al. | | |
| 2011/0247949 A1 * | 10/2011 | Yao | ............... | 206/305 |
| 2012/0080330 A1 * | 4/2012 | Rush et al. | ............... | 206/305 |
| 2014/0319149 A1 * | 10/2014 | Freedman | ............. | B65D 25/04 220/528 |
| 2016/0001927 A1 * | 1/2016 | Lucas, Jr. | ............. | B65D 25/02 206/204 |
| 2016/0031627 A1 * | 2/2016 | Yeh | ............... | B65D 81/266 206/204 |
| 2017/0108486 A1 * | 4/2017 | Joseph | ............. | G01N 33/48778 |
| 2017/0166387 A1 * | 6/2017 | Yao | ............... | B65D 83/0829 |
| 2017/0231604 A1 * | 8/2017 | Jakobsen | ........... | A61B 10/0096 422/536 |

OTHER PUBLICATIONS

Written Opinion of the International Searching Authority; PCT/EP2012/004846; dated Mar. 8, 2013; 6 pages.

* cited by examiner

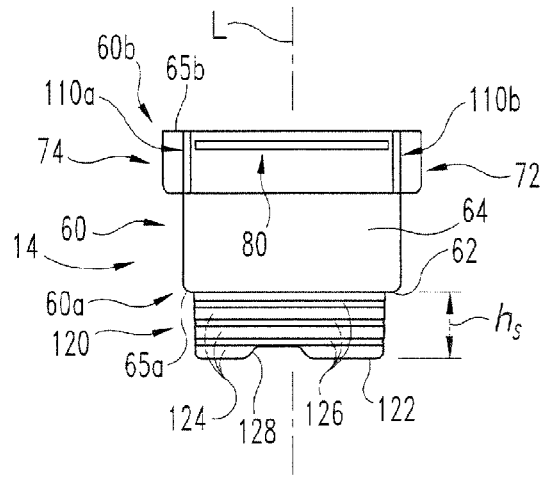
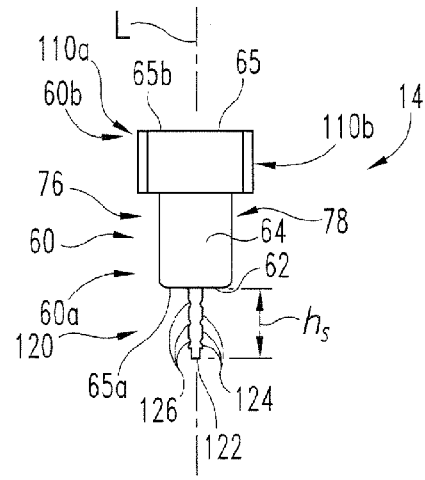
Fig. 5
Fig. 6
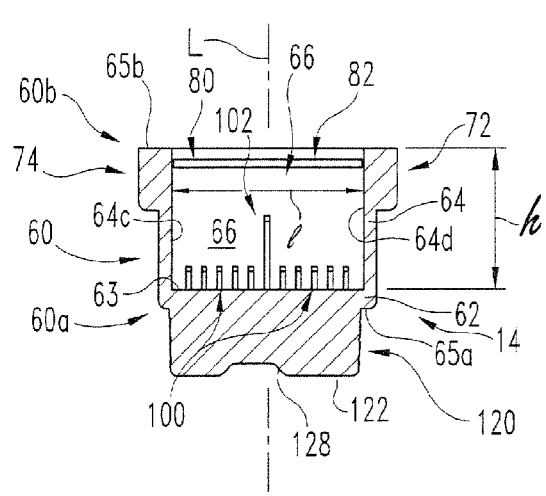
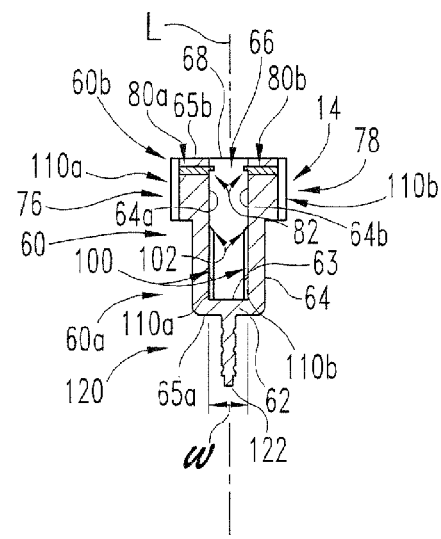
Fig. 7
Fig. 8

STORAGE CONTAINER FOR BIOSENSOR TEST ELEMENTS

FIELD OF THE INVENTION

This application generally relates to an improved storage container for biosensor test elements, and more particularly relates to a storage container for containing and maintaining blood glucose test strips.

BACKGROUND

As the number of patients suffering from diabetes and similar medical conditions increases, self-monitoring of blood glucose wherein the patient monitors his or her blood glucose levels has become common practice. The purpose of monitoring the blood-glucose level is to determine the concentration level and then to take corrective action, based upon whether the level is too high or too low, to bring the level back within a normal range. The failure to take corrective action can have serious medical implications. Glucose monitoring is a fact of everyday life for diabetic individuals, and the accuracy of such monitoring can literally mean the difference between life and death. Failure to test blood glucose levels accurately and on a regular basis can result in serious diabetes-related complications, including cardiovascular disease, kidney disease, nerve damage and blindness.

People with diabetes who intensively manage their blood sugar experience long-lasting benefits. The Diabetes Control and Complications Trial (DCCT) was a clinical study conducted from 1983 to 1993 by the National Institute of Diabetes and Digestive and Kidney Diseases (NIDDK). The DCCT compared intensive to conventional treatments. Patients on intensive treatment kept glucose levels as close to normal as possible with at least three insulin injections a day or an insulin pump, and frequent self-monitoring of blood glucose. Intensive treatment aimed to keep hemoglobin A1c (HbA1c), which reflects average blood glucose over a 2- to 3-month period, as close to normal as possible. Conventional treatment consisted of one or two insulin injections a day with once-a-day urine or blood glucose testing. The results of the DCCT study showed that keeping blood glucose levels as close to normal as possible slows the onset and progression of eye, kidney, and nerve diseases caused by diabetes. In fact, it demonstrated that any sustained lowering of blood glucose helps, even if the person has a history of poor control.

A number of biosensors, such as glucose meters, are currently available that permit an individual to test the glucose level in a small sample of blood. Many of the meter designs currently available make use of a disposable test element which, in combination with the meter, measures the amount of glucose in the blood sample electrochemically or optically. In current glucose meters, the information displayed as a consequence of a successful blood glucose measurement is the respective blood glucose value, typically shown in mg/dL or mmol units, and perhaps the time and date the measurement was performed. This information, in combination with calculation of planned or known intake of carbohydrates or planned or known activities and knowledge of other situational or individual factors, is in most cases sufficient to allow diabetics to adjust or derive their dietary intake and/or an immediate dose of insulin to inject to control blood glucose level on the short-term. Also, in case of low glucose values, diabetics can detect the need for intake of sugar to avoid hypoglycemia.

People with type 1 diabetes might perform an average of 5 to 10 blood glucose tests per day, the likes of which constitute a significant amount of time every day dedicating to blood glucose testing. Accordingly, the total test time, reliability of the test strips to provide an accurate blood glucose metering, portability and reliability of the container which contains the test elements, and ease of use in the retrieval of individual test elements are important considerations.

Current storage containers are designed and built to accommodate a single size test element, or as a "one size fits all" solution, both of which present inherent disadvantages. As should be appreciated, storage containers that are designed and built to accommodate a single size test element lead to increased container manufacturing and inventory costs. Additionally, current "one size fits all" storage containers are prone to cumbersome loading of the test elements, inadvertent or accidental spillage of the test elements which may lead to contamination and unreliability, and/or do not allow for easy access and removal of a single test element by the user. Additionally, current storage containers commonly have a circular vial form factor which presents portability and/or handling concerns.

Given the ramifications of accurate recording, reporting and analyzing of blood glucose measurements, improvements in the storage containers for storing and distributing test elements used to meter blood glucose are desired.

SUMMARY

In one form of the invention, a component for a storage container is provided which is configured to receive vertically oriented articles. The component includes a tubular sidewall extending longitudinally from a base, with the sidewall including an inner surface and an outer surface, and the base including a support surface and an underside. The component further includes at least one spacer portion extending from the underside of the base and configured for engagement with an interior surface of a corresponding storage container. The component also includes at least one pair of retainer elements extending laterally from the inner surface of the sidewall and inwardly into an interior region of the component, and with the retainer elements being oppositely oriented and configured to retain a vertically oriented article therebetween by frictional engagement with opposite longitudinal edges of the article. Each of the retainer elements comprises a tip portion sized and shaped to engage a corresponding one of the longitudinal edges of the article, and the retainer elements are sized and shaped for resilient deflection during insertion and removal of the article therebetween. The retainer elements are spaced apart to removably receive the article therebetween having a nominal width between the opposite longitudinal edges, and the retainer elements are adjustable relative to one another to define a variable separation distance or angular orientation therebetween for engagement with a different vertically oriented article defining a different nominal width between opposite longitudinal edges thereof, and wherein an insertion force for resilient deflection of the retainer elements during insertion of the article is less than a removal force for resilient deflection of the retainer elements during removal of the article.

In another form of the invention, a storage container for biosensor test elements is provided. The storage container includes a container component having a tubular sidewall defining an interior region extending generally along a longitudinal axis with a plurality of biosensor test elements contained within the interior region, and at least one retainer element extending laterally from an inner surface of the tubular sidewall and inwardly into the interior region, with each of the retainer elements having a tip portion positioned within the interior region and engaged with longitudinal edges of the biosensor test elements, and the tip portion sized and shaped to engage the longitudinal edges of the biosensor test elements during insertion of one or more of the biosensor test elements into the interior region whereby the insertion occurs via application of an insertion force, and the tip portion is sized and shaped to engage the longitudinal edges of the biosensor test elements during removal of one or more of the biosensor test elements from the interior region whereby the removal occurs via application of a removal force that is greater than the insertion force.

In a further form of the invention, a storage container for biosensor test elements is provided. The storage container includes a primary container component defining an inner chamber arranged generally along a longitudinal axis, and an insert container component positioned within the inner chamber of the primary container component and defining an interior region extending generally along the longitudinal axis for containing a plurality of the biosensor test elements. The insert container component includes a main body portion defining the interior region and further includes a spacer portion extending axially from the main body portion and having an adjustable height dimension. The spacer portion is positioned in abutment against an adjacent portion of the primary container component to position the insert container component at a select height within the inner chamber of the primary container component.

In yet another form of the invention, a storage container for biosensor test elements is provided. The storage container includes a container component having a tubular sidewall defining an interior region arranged generally along a longitudinal axis for containing a plurality of biosensor test elements, with the interior region having an overall height dimension, an overall width dimension, and an overall length dimension. The container component includes a plurality of divider elements extending inwardly from the tubular sidewall into the interior region and offset from one another along the overall length dimension, and with the divider elements extending along no more than one-half of the overall height dimension or across less than the overall width dimension, and the divider elements are configured for engagement with the biosensor test elements to aid in maintaining the biosensor test elements in a substantially upright orientation within the interior region.

Further aspects, embodiments, forms, features, benefits, objects, and advantages shall become apparent from the detailed description and figures provided herewith.

BRIEF DESCRIPTION OF THE FIGURES

FIG. 5 is a side elevational view of the insert component illustrated in FIG. 4.

FIG. 6 is an end elevational view of the insert component illustrated in FIG. 4.

FIG. 7 is a cross sectional view of the insert component illustrated in FIG. 4, as taken along line 7-7 of FIG. 4.

FIG. 8 is a cross sectional view of the insert component illustrated in FIG. 4, as taken along line 8-8 of FIG. 4.

DETAILED DESCRIPTION OF THE ILLUSTRATED EMBODIMENTS

Figure 1:
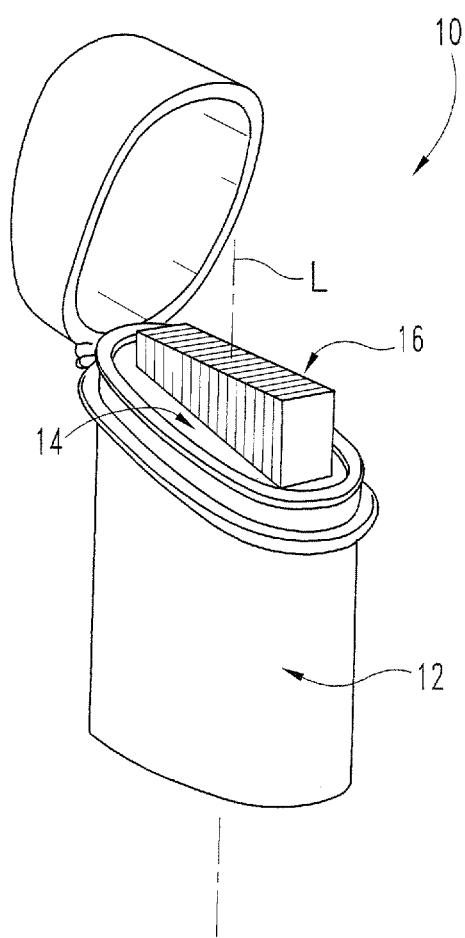
FIG. 1 is a perspective view of a storage container for biosensor test elements according to one form of the present invention.

For purposes of promoting an understanding of the principles of the invention, reference will now be made to the embodiments illustrated in the drawings and specific language will be used to describe the same. It will nevertheless be understood that no limitation on the scope of the invention is hereby intended, such alterations and further modifications in the illustrated device, and such further applications of the principles of the invention as illustrated herein being contemplated as would normally occur to one skilled in the art to which the invention relates.

Various embodiments of the present invention relate to an easy to use storage container for biosensor test elements, and more particularly test strips for the monitoring of blood glucose levels. In one specific embodiment, the storage container includes a primary container component and an insert container component positioned within an interior region of the primary container component and including features that contain and retain biosensor test strips therein.

Figure 2:
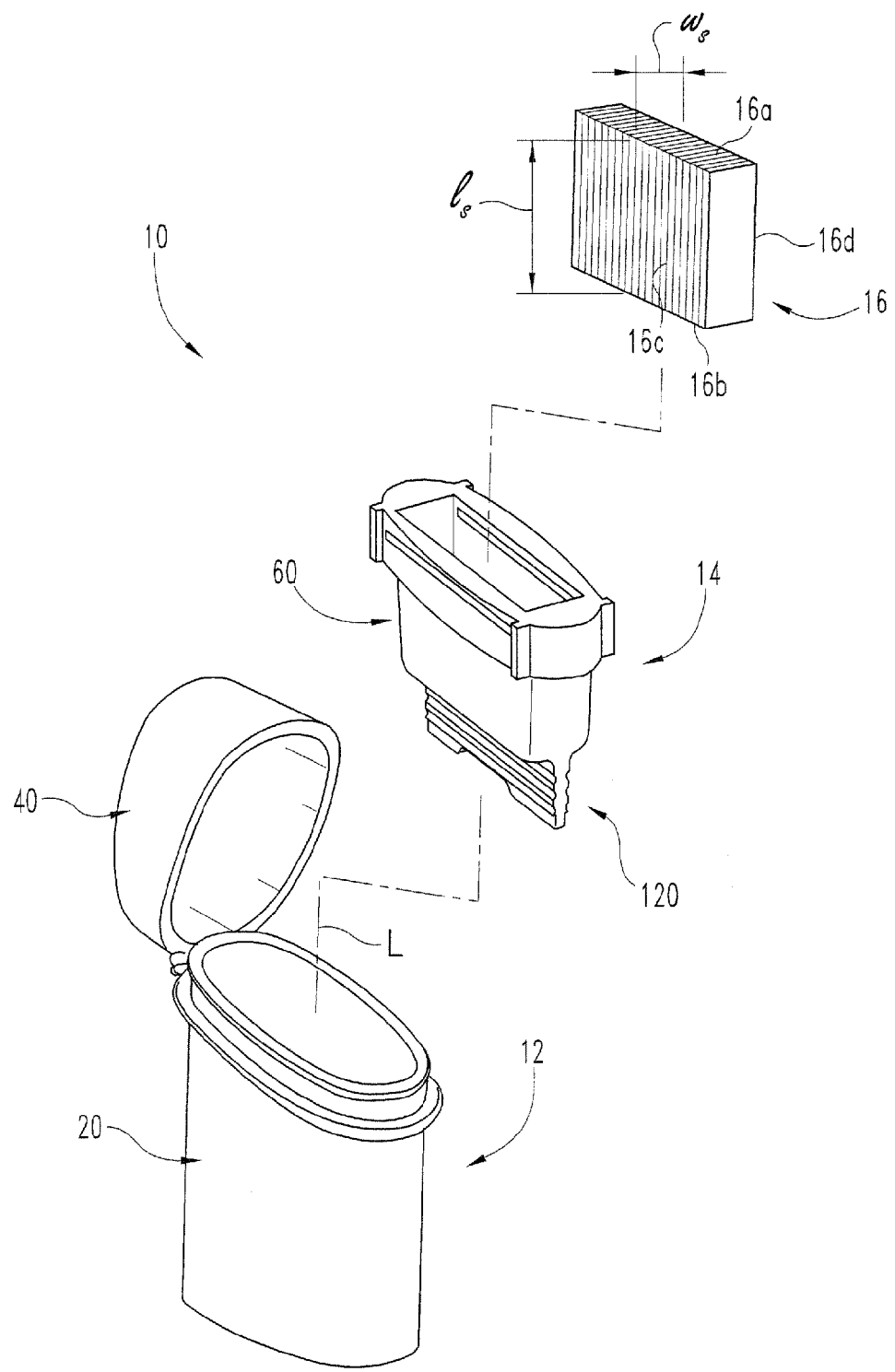
FIG. 2 is an exploded perspective view of the storage container illustrated in FIG. 1.

Referring to FIGS. 1 and 2, shown therein is one form of a storage container 10 for containing and retaining a plurality of vertically oriented articles therein. The storage container 10 extends along a central longitudinal axis L and generally includes a primary container 12 and an insert or liner component 14 positioned within an interior region of the primary container 12 and configured to contain and retain a plurality of vertically oriented articles 16 therein. In one embodiment, the primary container 12 and the insert component 14 are each formed of a polymeric or plastic material including, for example, polypropylene or polyethylene. However, other suitable materials are also contemplated including, for example, composite materials or metallic materials.

In one embodiment, the vertically oriented articles 16 contained within the storage container 10 are biosensor test elements configured to measure glucose levels in blood when used in association with a blood glucose meter (not shown) or other suitable measurement devices. In one specific embodiment, the biosensor test elements 16 are provided as electrochemical test strips that are useable with a blood glucose meter to perform a blood glucose measurement utilizing electrochemical techniques. In the illustrated embodiment, the test strips 16 have a rectangular shape and include opposite end edges 16a, 16b defining a relatively uniform strip length $l_s$, and opposite side or longitudinal edges 16c, 16d defining a relatively uniform strip width $w_s$ extending along the strip length $l_s$. However, test strips having other suitable shapes and configurations are also contemplated. Additionally, although the storage container 10 is illustrated and described for use in association with blood glucose (bG) test strips, it should be understood that the storage container 10 may also be used to store other types and configurations of biosensor test elements in lieu of or in addition to the biosensor test strips 16. Additionally, the storage container 10 may be used to store other types of analytical elements, diagnostic devices or other medical or pharmacological devices.

In one embodiment, the test strips 16 may perform blood glucose measurements utilizing electrochemical techniques. In another embodiment, the test strips 16 may perform blood glucose measurements utilizing optical techniques. One example of a test strip 16 configured for use with electrochemical measurement techniques is the ACCU-CHEK® Aviva test strip, as described in U.S. Patent Application Publication No. 2005/0016844, the contents of which are hereby incorporated herein by reference in their entirety. One example of a test strip 16 configured for use with optical measurement techniques is the ACCU-CHEK® Compact test strip, as described in U.S. Pat. No. 7,008,799, the contents of which are hereby incorporated herein by reference in their entirety. Each of these exemplary test strips are distributed in the United States by Roche Diagnostics Corporation of Indianapolis, Ind. Further details and examples of conventional blood glucose meters and related electrical and optical components and their respective measurement techniques are described in U.S. Pat. Nos. 5,352,351; 4,999,482; 5,438,271; 6,645,368; 5,997,817; 6,662,439; RE 36,268; 5,463,467; 5,424,035; 6,055,060; 6,906,802; and 5,889,585; the contents of which are hereby incorporated herein by reference in their entirety.

A desiccant can optionally be used in association with the storage container 10 to eliminate or reduce the humidity or moisture content within the interior region of the storage container 10 to preserve the integrity of the biosensor test strips 16 and/or to keep the partial pressure of water vapor relatively low compared to ambient conditions. More specifically, a desiccant may be incorporated directly into the storage container 10 and/or may be provided anywhere within the interior region of the storage container 10. In one embodiment, one or more portions of the primary container 12 and/or one or more portions of the insert component 14 may be partially or entirely formed from an injection moldable desiccant material. For example, in one specific embodiment, one or more of the walls of the primary container 12 and/or one or more walls of the insert component 14 may be formed from a desiccant-entrained polymer material, although other suitable configurations and materials are also contemplated. In other embodiments, a separate desiccant element or component may be placed within the interior region of the storage container 10 and in communication with the biosensor test strips 16 including, for example, a desiccant packet or sachet, a desiccant canister, a desiccant pellet or pellets, a particulate material including a desiccant, or other elements or structures including a desiccant. It should be understood that various types and compositions of desiccant are contemplated for use in association with the storage container 10 including, for example, porous paper, cellulosic fiber, a desiccant entrained polymer, porous plastic, molecular sieves, silica gels, clays, starches, calcium sulfate, calcium oxides and/or calcium chloride, just to name a few non-limiting possibilities.

In one form of the present invention, various types, sizes and configurations of the insert component 14 may be used interchangeably with the primary container 12 to accommodate a variety of types, sizes and configurations of the biosensor test strips 16. As should be appreciated, manufacturing costs and inventory levels associated with this arrangement of the storage container 10 may be significantly reduced due to the fact that one type/size of the primary container 12 may be used in association with multiple types/sizes of the insert component 14. In another form of the present invention, the insert component 14 may be provided as a disposable component that is discarded when the insert component 14 no longer contains any of the biosensor test strips 16, and a new insert component 14 containing a new set of biosensor test strips 16 may be positioned within the primary container 12. Alternatively, the insert component 14 can simply be refilled with a new set of biosensor test strips 16.

Figure 3:
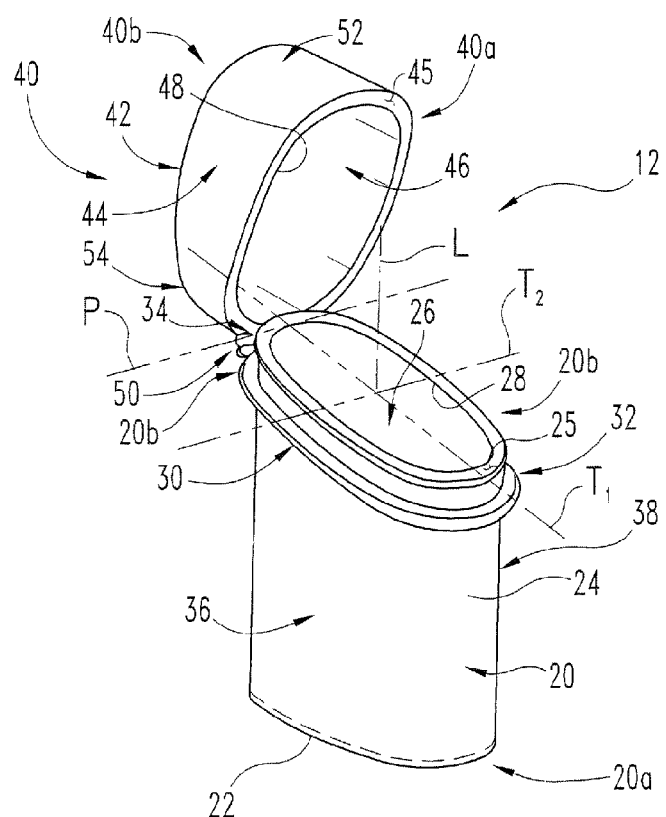
FIG. 3 is a perspective view of a primary container according to one embodiment of the present invention for use in association with the storage container illustrated in FIG. 1.
Figure 4:
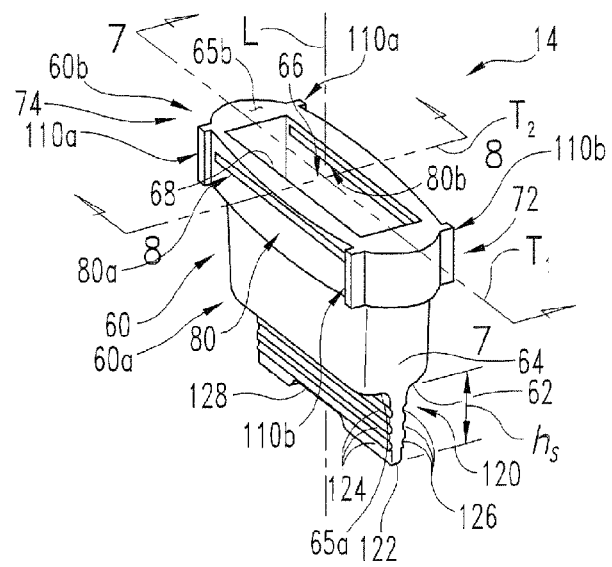
FIG. 4 is a perspective view of an insert component according to one embodiment of the present invention for use in association with the storage container illustrated in FIG. 1.

Referring to FIG. 3, shown therein is the primary container 12 according to one embodiment of the present invention. The primary container 12 has a height extending along the longitudinal axis L and generally includes a body 20 and a removable cap 40 movably attached to the body 20.

In the illustrated embodiment, the body 20 has a lower end portion 20a and an upper end portion 20b, and generally includes a substantially planar bottom wall or base 22 adjacent the lower end portion 20a, and a tubular sidewall 24 extending axially from the bottom wall 22 toward the upper end portion 20b and defining a top or upper surface 25. The bottom wall 22 and the sidewall 24 together define a cylindrical configuration extending generally along the longitudinal axis L and having an inner chamber 26 defining an upper dispensing opening 28 adjacent the upper end portion 20b. The body 20 may also include a shoulder or lip 30 extending annularly about the sidewall 24 adjacent the dispensing opening 28 for engagement with the cap 40 to close off the dispensing opening 28 and enclose the inner chamber 26. The body 20 may further include one or more sealing members such as, for example, a gasket, an o-ring or a sealable foil (not show) positioned on or adjacent the upper surface 25 or the shoulder 30 or along the bottom portion of the cap 40 to provide sealing engagement between the body 20 and the cap 40. The sealing members may be provided to establish a seal between the body 20 and the cap 40 to prevent moisture and/or containments from entering the interior region of the storage container 10, and/or to provide a hermetic seal to isolate the biosensor test strips 16 from the external environment. The sealing members may be formed of rubber, plastic, polymeric, synthetic or metallic materials. However, other suitable materials are also contemplated.

In the illustrated embodiment, the body 20 has an oblong form factor including an elongate dimension (i.e., a length) extending along a major transverse axis $T_1$ from a front portion 32 to a rear portion 34, and a transverse dimension (i.e., a width) extending along a minor transverse axis $T_2$ from a first side portion 36 to an opposite second side portion 38. In one embodiment, the major and minor transverse axes $T_1$, $T_2$ intersect one another at a central longitudinal axis L. In one specific embodiment, the body 20 has a generally oval or elliptical-shaped outer cross sectional profile. However, other oblong shapes and cross sections are also contemplated including, for example, a rectangular cross section, a curvilinear cross section, a polygonal cross section, or other suitable cross-sectional shapes and configurations. Alternatively, the body 20 may be provided with a symmetrical form factor including, for example, a circular-cylindrical cross section, a square cross section, or other suitable symmetrical cross-sectional shapes and configurations. Additionally, in the illustrated embodiment, the body 20 has a first height adjacent the front portion 32 and a greater second height adjacent the rear portion 34 to thereby provide the body 20 of the primary container 12 with a varying height dimension. However, other embodiments are also contemplated wherein the body 20 is provided with a substantially uniform height.

In the illustrated embodiment, the removable cap 40 has a lower end portion 40a and an upper end portion 40b, and generally includes a substantially planar upper wall 42 adjacent the upper end portion 40b, and a tubular sidewall or skirt 44 extending from the upper wall 42 toward the lower end portion 40a and defining a bottom or lower surface 45. The upper wall 42 and the sidewall 44 together define a cylindrical configuration having an interior region 46 defining a lower lid opening 48 adjacent the lower end portion 40a. The cap 40 may also include an inner shoulder or lip (not shown) extending annularly about an inner surface of the sidewall 44 adjacent the lower lid opening 48 for engagement with the upper surface 25 defined by the sidewall 24 of the container body 20. The cap 40 serves to close off the dispensing opening 28 of the container body 20 and enclose the inner chamber 26 of the primary container 12. The cap 40 may further include one or more sealing members (not shown) such as, for example, a gasket, an o-ring or a sealable foil positioned on or adjacent the lower surface 45 (or the inner shoulder or lip) to provide sealing engagement between the body 20 and the cap 40. The sealing members may be formed of rubber, plastic, polymeric, synthetic or metallic materials. However, other suitable materials are also contemplated.

In one embodiment the cap 40 is attached to the body 20 via a flexible coupling element or hinge 50 that allows the cap 40 to pivot relative to the body 20 between an open position (FIG. 3) and a closed position (not shown). In this manner, the hinge 50 pivotally attaches the cap 40 to the body 20 to provide the primary container 12 with a flip-top configuration wherein the cap 40 is allowed to pivot about a pivot axis P between open and closed positions relative to the body 20. In the illustrated embodiment, the pivot axis P is arranged generally parallel with the minor transverse axis $T_2$ of the body 20. However, in other embodiments, the pivot axis P may be arranged generally parallel with the major transverse axis $T_1$ of the body 20, or may be arranged at an oblique angle relative to the major and/or minor transverse axes $T_1$, $T_2$. Other embodiments are also contemplated wherein the cap 40 is attached to the body 20 by other suitable attachment techniques, or still other embodiments wherein the cap 40 is separate from the body 20 until fully engaged to the body 20 in the closed position. When the cap 40 is in the open position, the upper dispensing opening 28 is unobstructed to provide ready access to the test strips 16 contained therein. When the cap 40 is in the closed position, the upper dispensing opening 28 is covered or closed off to isolate the inner chamber 26 from ambient conditions to protect and maintain the test strips 16 within the storage container 10 and/or to prevent moisture or contaminants from entering the storage container 10.

In the illustrated embodiment, the cap 40 has an oblong form factor that substantially corresponds to the oblong form factor illustrated and described above with regard to the body 20. In one embodiment, the cap 40 has an oval shape. However, other shapes are also contemplated including, for example, an elliptical shape or a rectangular shape. Alternatively, the cap 40 may be provided with a symmetrical form factor including, for example, a circular cylindrical shape, a square shape, or other suitable shapes or configurations. Additionally, in the illustrated embodiment, the cap 40 has a first height adjacent a front portion 52 and a lesser second height adjacent a rear portion 54 to thereby provide the cap 40 with a varying cap height. However, other embodiments are also contemplated wherein the cap 40 is provided with a substantially uniform height. As should be appreciated, when the cap 40 is in the closed position and engaged with the body 20, the varying height of the cap 40 cooperates with the varying height of the body 20 to provide the primary container 12 with a substantially uniform overall height profile. In some embodiments, the body 20 and the cap 40 are provided with features that cooperate with one another to provisionally maintain the cap 40 in the closed position to prevent or inhibit inadvertent opening of the cap 40. For example, the body 20 and the cap 40 may be provide with detent features, interlocking features, snap features, or fastening features that provisionally maintain the cap 40 in the closed position relative to the body 20. Additionally, variations in the engagement arrangement between cap 40 and the body 20 are also contemplated. For example, in alternative embodiments, the cap 40 can be configured to engage the body 20 via a threaded arrangement, a twist lock arrangement, a bayonet lock arrangement, a friction fit arrangement, or other suitable engagement arrangements. In another alternative embodiment, the cap 40 may be provided with a passage (not shown) extending therethrough and communicating with the inner chamber 26 of the body 20, and with a closing member (not shown) cooperating with the passage such that one or more of the test strips 16 can be removed from the inner chamber 26 without having to disengage the cap 40 from the body 20. The closing member may be in the form of a plug, valve, or other suitable closeable access devices.

Referring collectively to FIGS. 4-8, shown therein is the insert component 14 according to one embodiment of the present invention. As indicated above, the insert component 14 is positioned within the inner chamber 26 in the body 20 of the primary container 12, and is configured to contain and retain a plurality of the biosensor test strips 16 therein. As will be discussed in greater detail below, in one embodiment, the insert component 14 is generally designed to accommodate test strips 16 having varying sizes (e.g., varying test strip lengths and widths). In other embodiments, various sizes and configurations of the insert component 14 may be provided which are interchangeable with the primary container 12 such that the same primary container 12 may be used to universally/interchangeably receive various sizes and configurations of the insert component 14, which in turn receives a particular size and configuration of the test strips 16 therein.

In the illustrated embodiment, the insert component 14 has a height extending along the longitudinal axis L and generally includes a main body 60 having a lower end portion 60a and an upper end portion 60b, and a spacer portion 120 extending axially from the lower end portion 60a of the main body 60. As will be discussed in greater detail below, the main body 60 includes an interior region configured to receive and maintain the test strips 16 therein, and the spacer portion 120 rests against the bottom wall 22 of the primary container 12 to position the main body 60 (and the test strips 16 contained therein) at a select height relative to the primary container 12. In one embodiment, the main body 60 and the spacer portion 120 are formed integral with one another to define a single-piece monolithic structure. However, other embodiments are also contemplated where the main body 60 and the spacer portion 120 comprise separate structures that are couple together via fastening, pinning, fusing, welding, adhering, or other suitable attachment methods to form an integrated insert component 14. Additionally, in other embodiments, the insert component 14 need not necessarily include a spacer portion 120.

In the illustrated embodiment, the main body 60 has a height extending along the longitudinal axis L, a length extending generally along a first transverse axis $T_1$, and a width extending generally along a second transverse axis $T_2$. The main body 60 further includes a substantially planar bottom wall or base 62 defining an inner support surface 63 and an underside 65a, and a tubular sidewall 64 extending axially from the bottom wall 62 toward the upper end portion 60b and defining a top or upper end surface 65b. The bottom wall 62 and the sidewall 64 together define a cylindrical configuration extending generally along the longitudinal axis L and having an interior region 66 defining an upper dispensing opening 68 at the upper end surface 65b.

As will be discussed in greater detail below, the main body 60 may be provided with a number of retainer elements 80 (FIGS. 7-9) including tip portions 82 extending inwardly from an inner surface of the sidewall 64 and laterally into the interior region 66 in the direction of the second transverse axis $T_2$, and also extending along the length of the sidewall 64 in the direction of the first transverse axis $T_1$, with the tip portions 82 positioned and configured for engagement with the biosensor test strips 16 to aid in retaining the test strips 16 within the interior region 66 of the main body 60. The main body 60 may also be provided with a series of low profile divider elements or lateral projections 100 (FIGS. 7 and 8) extending inwardly from an inner surface of the sidewall 64 and into the interior region 66 in the direction of the second transverse axis $T_2$, and also extending along the height of the sidewall 64 in the direction of the longitudinal axis L for engagement with the biosensor test strips 16 to aid in maintaining the test strips 16 in a substantially vertical orientation within the interior region 66 of the main body 60. The main body 60 may be further provided with one or more locking ribs or splines 110 (FIGS. 4-6) extending outwardly from an outer surface of the sidewall 64 in the direction of the second transverse axis $T_2$, and also extending along the height of the sidewall 64 in the direction of the longitudinal axis L for retentional engagement with an inner surface of the primary container 12 to aid in retaining the insert component 14 within the inner chamber 26 of the primary container 12.

In the illustrated embodiment, the main body 60 of the insert component 14 has an oblong form factor that substantially corresponds to the oblong form factor defined by the body 20 of the primary container 12, including a depth dimension extending along a major axis corresponding to the first transverse axis $T_1$ from a front portion 72 of the main body 60 to a rear portion 74 of the main body 60, and a width dimension extending along a minor axis corresponding to the second transverse axis $T_2$ from a first side portion 76 to an opposite second side portion 78. In one embodiment, the major and minor transverse axes intersect one another at the central longitudinal axis L. In the illustrated embodiment, the main body 60 has a generally oval-shaped cross section. However, other oblong shapes and cross sections are also contemplated including, for example, an elliptical cross section, a rectangular cross section, a curvilinear cross section, a polygonal cross section, or other suitable oblong cross-sectional shapes and configurations. Alternatively, the main body 60 may be provided with a symmetrical form factor including, for example, a circular-cylindrical cross section, a square cross section, or other suitable symmetrical cross-sectional shapes and configurations. Additionally, the insert component 14 may be provided with a height profile that generally corresponds to the height profile of the primary container 12 wherein the upper surface 65b of the main body 60 of the insert component 14 is arranged substantially flush with the upper surface 25 of the body 20 of the primary container 12 (FIG. 1). However, in other embodiments, the upper surface 65b of the main body 60 may be recessed below or elevated above the upper surface 25 of the body 20. Still other embodiments are also contemplated wherein the insert component 14 is provided with a substantially uniform height profile and/or a height profile that does not correspond with the height profile of the body 20 of the primary container 12.

As indicated above, in one embodiment, the main body 60 of the insert component 14 includes a number of retainer elements 80 (FIGS. 7-9) including tip or end portions 82 extending laterally from an inner surface of the sidewall 64 and inwardly into the interior region 66 of the main body 60 in the direction of the second transverse axis $T_2$, and also extending along the length of the sidewall 64 in the direction of the first transverse axis $T_1$, with the tip portions 82 of the retainer element 80 positioned and configured for frictional engagement with the biosensor test strips 16 to aid in retaining the test strips 16 within the interior region 66 of the main body 60. In the illustrated embodiment, the retainer elements 80 are sized, configured and positioned for frictional engagement with the longitudinal side edges 16c, 16d of the biosensor test strips 16 to aid in retaining/securing the test strips 16 within the interior region 66 of the main body 60 to prevent accidental spillage and/or unintended removal of the test strips 16 from the interior region 66. However, the retainer elements 80 provide relatively unrestricted access to the test strips 16 for retrieval of one or more of the test strips 16 from the storage container 10, and further provide less restrictive insertion of the test strips 16 into the interior region 66 of the insert component 14 to facilitate loading of the test strips 16 into the storage container 10. In one embodiment, the retainer elements 80 are sized, configured and positioned to provide a lower strip insertion force compared to a higher strip retrieval force, the likes of which will be discussed in greater detail below.

In the illustrated embodiment, the insert component 14 is provided with an opposing pair of the retainer elements 80a, 80b (FIG. 8) that are recessed below the upper end surface 65b of the main body 60 and arranged on opposite sides of the interior region 66 for frictional engagement with oppositely facing side edges 16c, 16d of the biosensor test strips 16. However, it should be understood that other embodiments are also contemplated, including embodiments where the insert component 14 is provided with a second opposing pair of the retainer elements that are axially offset from the first opposing pair of retainer elements 80a, 80b in a direction along the longitudinal axis L toward the lower end portion 60a of the main body 60. In other embodiments, the insert component 14 may be provided with additional opposing pairs of the retainer elements 80a, 80b that are offset from one another in a direction along the vertical longitudinal axis L.

Figure 9A:
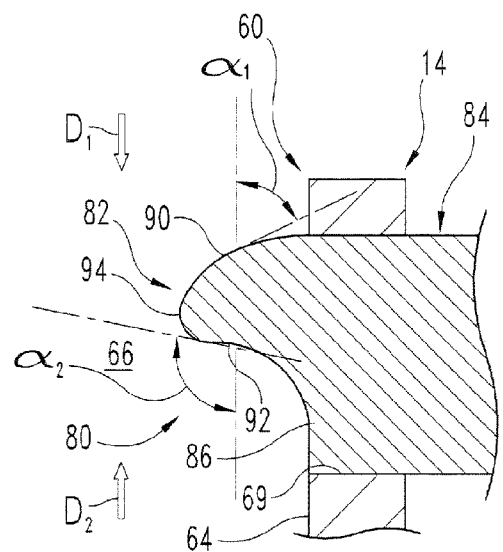
FIG. 9A is an enlarged cross sectional view of one embodiment of a retainer element for use in association with the insert component illustrated in FIG. 4.

Referring to FIG. 9A, shown therein is an enlarged view of the retainer element 80. It should be understood that the retainer elements 80a, 80b are mirror images of one another relative to the vertical longitudinal axis L, and that the features and aspects associated with the retainer element 80 apply to both of the retainer elements 80*a*, 80*b*. In the illustrated embodiment, the retainer elements 80 each include a mounting portion 84 positioned within corresponding lateral openings 69 formed in the sidewall 64 of the main body 60, with the tip or end portion 82 extending into the interior region 66 of the main body 60 for frictional engagement with a corresponding one of the longitudinal side edges 16*c*, 16*d* of the test strips 16. The distance separating the tip portions 82 of the retainer elements 80*a*, 80*b* and/or the angle at which the retainer elements 80*a*, 80*b* extend into the interior region 66 of the main body 60 may be adjusted to accommodate test strips 16 having different strip widths $w_s$ (i.e., the nominal width dimension between the longitudinal side edges 16*c*, 16*d*). Such adjustment of the distance separating the tip portions 82 of the retainer elements 80*a*, 80*b* and/or the angular orientation of the retainer elements 80*a*, 80*b* may be accomplished by varying the position and/or angular orientation of the retainer elements 80*a*, 80*b* relative to the insert component 14, or by removing and replacing the retainer elements 80*a*, 80*b* with retainer elements having a different configuration defining a different separation distance and/or angular orientation relative to the insert component 14 to accommodate test strips 16 having different nominal strip widths $w_s$ between the longitudinal edges 16*c*, 16*d*.

As indicated above, the retainer elements 80 each include a tip or end portion 82 extending into the interior region 66 of the main body 60 for frictional engagement with the longitudinal side edges 16*c*, 16*d* of the test strips 16, and a mounting portion 84 positioned within a corresponding lateral opening 69 formed in the sidewall 64 of the main body 60 of the insert component 14. The retainer element 80 may be secured to the main body 60 via fastening, pinning, fusing, welding, adhering, or other suitable attachment techniques. Additionally, as indicated above, the distance separating the tip portions 82 of the retainer elements 80*a*, 80*b* and/or the angle at which the retainer elements 80*a*, 80*b* extend into the interior region 66 of the main body 60 may be adjusted to accommodate test strips 16 having different nominal strip widths $w_s$. It should be appreciated that the retainer elements 80*a*, 80*b* may be designed to be adjustable relative to the insert component 14 (i.e., adjustable position and/or orientation), or designed for disengagement and removal from the insert component 14 for replacement by a different configuration of the retainer elements 80*a*, 80*b* to accommodate test strips 16 having different nominal strip widths $w_s$.

Figure 9B:
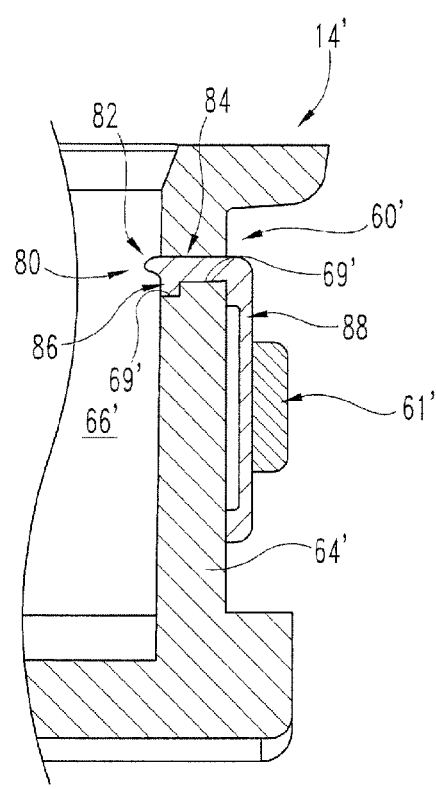
FIG. 9B is a cross sectional view of one embodiment of a retainer element attached to an insert component.

Referring to FIG. 9B, shown therein are further details of the retainer element 80, as attached to the sidewall 64' of the main body 60' of an insert component 14'. As indicated above, the retainer element 80 includes a tip or end portion 82 and a mounting portion 84, with the tip portion 82 extending laterally from an inner surface of the sidewall 64' and inwardly into the interior region 66' of the main body 60' for engagement with the biosensor test strips 16 (not shown). The mounting portion 84 is positioned within a corresponding lateral opening 69' formed in the sidewall 64' of the main body 60' of the insert component 14'. The mounting portion 84 includes a lip 86 extending generally along the longitudinal axis L and arranged substantially flush with the inner surface of the sidewall 64'. The lip 86 provides additional support and structural integrity to the retainer element 80 and facilities secure engagement with the sidewall 64' of the main body 60'. The mounting portion 84 further includes an axial flange 88 positioned along an exterior surface of the sidewall 64' of the main body 60' and extending generally along the longitudinal axis L to provide additional support and structural integrity to the retainer element 80 and to further facilitate secure engagement with the sidewall 64' of the main body 60'. The main body 60' of the insert component 14' may be provided with a clip or locking element 61' that is selectively engagable with the axial flange 88 to maintain the retainer element 80 in secure engagement with the insert component 14'. As indicated above, the retainer element 80 may be designed to be adjustable relative to the insert component 14 (i.e., adjustable position and/or orientation), or designed for disengagement and removal from the insert component 14 for replacement by a different configuration of the retainer elements 80 to accommodate test strips 16 having different nominal strip widths $w_s$. Although a specific configuration of the retainer elements 80 has been illustrated and described herein, it should be understood that other configurations of the retainer element 80 and other suitable techniques for attaching the retainer element 80 to the insert container component are also contemplated as falling within the scope of the present invention.

Referring once again to FIG. 9A, in the illustrated embodiment of the retainer element 80, the tip portion 82 includes an upper surface 90 and a lower surface 92 that are each tapered at an oblique angle relative to the longitudinal axis L. Additionally, in a more specific embodiment, the upper and lower surfaces are each rounded, and the tip portion 82 may further include a rounded distal end surface 94 extending between the upper and lower surfaces 90, 92. The upper and lower surfaces 90, 92 and the end surface 94 cooperate with one another to provide the retainer element 80 with a fin-shaped outer profile. In the illustrated embodiment, the rounded upper surface 90 is provided with a relatively steep taper angle $\alpha_1$ (e.g., 50° from the vertical longitudinal axis L) to facilitate relatively unobstructed and less restrictive loading of the test strips 16 into the interior region 66 of the main body 60, and the rounded lower surface 92 is provided with a relatively shallower taper angle $\alpha_2$ (e.g., 105° from the vertical longitudinal axis L) to retain/secure the test strips 16 within the interior region 66 of the main body 60 to prevent accidental spillage and/or unintended or involuntary removal of the test strips from the storage container 10. In one embodiment of the retainer element 80, the rounded upper surface 90 and the distal end surface 94 each have a convex profile, while the rounded lower surface 92 has a concave profile. Additionally, in the illustrated embodiment, the tip portion 82 has an overall height measured between the upper and lower surfaces 90, 92 of approximately 0.26 mm, and an overall width measured from the inner surface of the sidewall 64 of the main body 60 to the distal-most end of the retainer element 80 of approximately 0.50 mm. However, it should be understood that the shape/configuration of the retainer element 80 and the height/width dimensions are exemplary in nature, and that other shapes, configurations and sizes of the retainer element 80 are also contemplated as falling with the scope of the present invention.

As a result of the shape and configuration of the retainer elements 80*a*, 80*b*, the test strips 16 may be loaded into the interior region 66 of the main body 60 via a relatively low strip insertion force to enhance or facilitate loading of the test strips 16 into the storage container 10, while the test strips 16 are retained within the interior region 66 of the main body 60 via a relatively higher removal or retrieval force to prevent accidental spillage and/or unintended or involuntary removal of the test strips 16 from the storage container 10. Additionally, the retainer elements 80*a*, 80*b* are sized and shaped for resilient deflection during insertion and during removal of the test strips 16 into/from the interior region 66. Moreover, frictional engagement of the tip or end portions 82 of the retainer elements 80a, 80b with the longitudinal side edges 16c, 16d of the test strips 16 aids in maintaining the test strips 16 in a substantially vertical orientation within the storage container 10 so as to maintain the upper end portions of the test strips 16 in a position that allows for easy access and grasping of an individual test strip 16 by the user to facilitate removal of a selected test strip from the storage container 10. The retainer elements 80a, 80b also allow relatively free uninhibited movement of the test strips 16 in a first direction $D_1$ (i.e., in a downward direction along the longitudinal axis L toward the bottom wall 62) to facilitate insertion or loading of the test strips 16 into the storage container 10, while inhibiting or restricting movement of the test strips 16 in an opposite second direction $D_2$ (i.e., in an upward direction along the longitudinal axis L toward the dispensing opening 68) to retain/secure the test strips 16 within the storage container 10.

Figure 10:
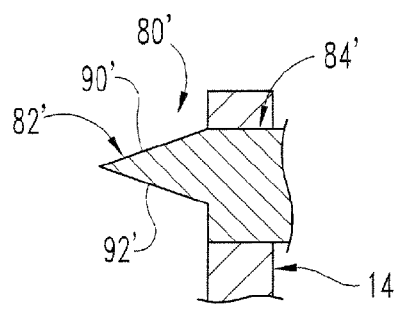
FIG. 10 is an enlarged cross sectional view of another embodiment of a retainer element for use in association with the insert component illustrated in FIG. 4.

As indicated above, although the retainer elements 80 have been illustrated and described as having a particular shape and configuration, other shapes and configurations are also contemplated. For example, as illustrated in FIG. 10, another embodiment of a retainer element 80' is illustrated for use in association with the storage container 10. The retainer element 80' may be configured similar to the retainer element 80, including a tip or end portion 82' and a mounting portion 84'. However, unlike the tip portion 82 of the retainer element 80, the tip portion 82' of the retainer element 80' is provided with a triangular-shaped outer profile including a tapered upper surface upper surface 90' and a tapered lower surface 92'. Although the tapered upper and lower surfaces 90', 92' are illustrated as being generally symmetrical to one another and defining substantially equal taper angles, it should be understood that other non-symmetrical embodiments are also contemplated wherein the tapered upper and lower surfaces 90', 92' may be provided with different taper angles.

Figure 11:
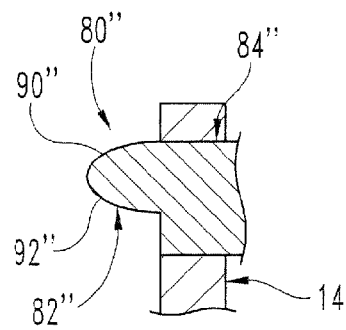
FIG. 11 is an enlarged cross sectional view of a further embodiment of a retainer element for use in association with the insert component illustrated in FIG. 4.

Additionally, as illustrated in FIG. 11, shown therein is another embodiment of a retainer element 80" suitable for use in association with the storage container 10. The retainer element 80" may be configured similar to the retainer element 80, including a tip or end portion 82" and a mounting portion 84". However, unlike the tip portion 82 of the retainer element 80, the tip portion 82" of the retainer element 80" is provided with a oval-shaped or elliptical-shaped outer profile including a tapered upper surface upper surface 90" and a tapered lower surface 92". In the illustrated embodiment, the tapered upper surface 90" and the tapered lower surface 92" are each rounded and define a convex profile. However, other suitable shapes and configurations are also contemplated. Further, although the tapered upper and lower surfaces 90", 92" are illustrated as being generally symmetrical to one another and defining substantially equal taper angles, it should be understood that other non-symmetrical embodiments are also contemplated wherein the tapered upper and lower surfaces 90", 92" may be provided with different taper angles. It should be understood that other embodiments of retainer elements suitable for use in association with the storage container 10 are also contemplated, including retainer elements having end portions that are provided with outer profiles defining other shapes and configurations, including circular configurations, polygonal configurations, curvilinear configurations, or other suitable shapes and configurations.

As indicated above, the main body 60 of the insert component 14 may be provided with a series of low profile divider elements or lateral projections 100 (FIGS. 7 and 8) extending inwardly from an inner surface of the sidewall 64 and into the interior region 66 of the main body 60 along at least a portion of the overall width dimension w of the interior region 66 (i.e., the interior dimension between inner surfaces of the opposite first and second sides 64a, 64b of the sidewall 64). The divider elements 100 are offset from one another along the length dimension l of the interior region 66 (i.e., the interior dimension between opposite end walls 64c, 64d of the sidewall 64) and also extending along a least a portion of the overall height dimension of the interior region 66 (i.e., the interior dimension between the bottom support surface 63 of the bottom wall 62 and the upper surface 65b of the sidewall 64) for engagement with the biosensor test strips 16 to aid in maintaining the test strips 16 in a substantially upright orientation within the interior region 66 of the insert component 14 generally parallel with the longitudinal axis L.

In the illustrated embodiment, the low profile divider elements 100 extend across only a portion of the overall width dimension of the interior region 66 of the insert component 14 and do not extend across the entire width dimension w of the interior region 66. In one specific embodiment, the low profile divider elements 100 extend across less than one-half of the width dimension w of the interior region 66, and in a more specific embodiment extend across less than one-quarter of the width dimension w of the interior region 66. However, in other embodiments, the low profile divider elements 100 may extend substantially entirely across the width dimension w of the interior region 66.

In the illustrated embodiment, the low profile divider elements 100 extend from the support surface 63 of the bottom wall 62. However, in other embodiments, the low profile divider elements 100 may be offset from the support surface 63 of the bottom wall 62 (i.e., the low profile divider elements 100 may be spaced from the support surface 63), and may positioned at various elevations within the interior region 66. Additionally, in the illustrated embodiment, the low profile divider elements 100 extend along significantly less than the overall height dimension h of the interior region 66. In one specific embodiment, the low profile divider elements 100 extend along less than one-half of the height dimension h of the interior region 66, and in a more specific embodiment extend along less than one-quarter of the height dimension h of the interior region 66, and in a still more specific embodiment extend along less than one-eighth of the height dimension h of the interior region 66. However, in other embodiments, the low profile divider elements 100 may extend substantially entirely along the entire height dimension h of the interior region 66. Additionally, in some embodiments, the low profile divider elements 100 are provided with varying heights. For example, in the illustrated embodiment, the insert component 14 is provided with a number of high profile divider elements 102 extending inwardly from an inner surface of the sidewall 64 and into the interior region 66, and having a height that is greater than the height of low profile divider elements 100. In one embodiment, the high profile divider elements 102 are positioned in the central section of the interior region 66. However, other positions of the high profile divider elements 102 are also contemplated. In a specific embodiment, the high profile divider elements 102 extends along greater than one-half of the height dimension h of the interior region 66. However, other heights of the high profile divider elements 102 are also contemplated.

In the illustrated embodiment, a first set 100a of the low profile divider elements 100 extends laterally from a first sidewall 64a and into the interior region 66, and a second set 100b of the low profile divider elements 100 extends laterally from an opposite second sidewall 64b and into the interior region 66. However, in other embodiments, the low profile divider elements 100 may extend from only one of the first and second sidewalls 64a, 64b. In still other embodiments, the low profile divider elements 100 may extend from the support surface 63 of the bottom wall 62, but do not contact or extend from either of the first and second sidewalls 64a, 64b. In one embodiment, the first set 100a of the low profile divider elements are aligned in an opposing manner with the second set 100b of the low profile divider elements. However, in another embodiment, the first set 100a of the low profile divider elements may be offset from the second set 100b of the low profile divider elements (i.e., the first set 100a of the low profile divider elements may be aligned with the spaces or gaps between the second set 100b of the low profile divider elements).

As should be appreciated, the biosensor test strips 16 are positioned within the interior region 66 of the insert component 14 and are maintained in a substantially vertical orientation via the low profile divider elements 100 and/or the high profile divider elements 102 to prevent the test strips 16 from falling lengthwise into the interior region 66 as the number of test strips 16 contained within the interior region 66 is gradually decreased, yet the divider elements 100, 102 do not impede removal of individual strips from the interior region 66 by the user. Notably, since the divider elements 100, 102 extend across less than the entire width dimension of the interior region 66 and along less than the entire height dimension, the divider elements 100, 102 do not hinder or otherwise obstruct (either physically or visually) removal of the biosensor test strips 16 from the interior region 66. In essence, the divider elements 100, 102 act as stabilizers to maintain the test strips 16 in a substantially vertical or upright orientation and in a neat and compact arrangement within the insert component 14 for presentation to the user, while still allowing for easy access and removal of an individual test strip 16 from the insert component 14. Additionally, in order to facilitate loading of the test strips 16 into the interior region 66 of the insert component 14, the upper surfaces of the low profile divider elements 100 and/or the high profile divider elements 102 may be angled or tapered.

As indicated above, the main body 60 of the insert component 14 may be provided with one or more raised locking ribs or splines 110 (FIGS. 4-6) extending outwardly from an outer surface of the sidewall 64 in the direction of the second transverse axis $T_2$ and also extending along the height of the sidewall 64 in the direction of the longitudinal axis L for engagement with an inner surface of the body 20 of the primary container 12 to aid in maintaining the insert component 14 within the inner chamber 26 of the primary container 12. In the illustrated embodiment, the locking ribs 110 extend along less than the overall height profile of the main body 60, but may alternatively extend substantially entirely along the overall height profile of the main body 60. The locking ribs 110 are preferably located along an upper portion of the main body 60 to facilitate stability of the insert component 14 within the primary container 12, as well as to stabilize and/or strengthen the tubular sidewall 24 of the primary container 12 against inward deflection. The locking ribs 110 are preferably positioned below the seal region between the body 20 and the cap 40 of the primary container 12 to avoid interference with and/or distortion of the seal which might otherwise compromise the integrity of the seal. In the illustrated embodiment, the main body 60 includes a pair of locking ribs 110a, 110b extending outwardly from each of the opposite sidewalls of the insert component 14 and positioned adjacent the front and rear portions 32, 34. However, in other embodiments, the main body 60 may be provided with any number of the locking ribs 110 positioned along other portions of the main body 60. Additionally, the locking ribs 110 may be provided with a roughened or pointed tip portion 112 to facilitate secure locking engagement with the inner surface of the primary container 12 to securely maintain the insert component 14 within the inner chamber 26 of the primary container 12.

As indicated above, the insert component 14 may be provided with a spacer portion 120 (FIGS. 4-6) extending axially from the lower end portion 60a of the main body 60 and which abuts against the bottom wall 22 of the primary container 12 (or other portions of the primary container 12) to position the main body 60 (and the test strips 16 contained therein) at a select height relative to the primary container 12. In the illustrated embodiment, the spacer portion 120 comprises a flange or strut extending axially from the underside surface 65a defined by the bottom wall 62 of the main body 60. In one embodiment, the strut 120 has a substantially rectangular configuration and projects axially from the underside 65a of the bottom wall 62 generally along the longitudinal axis L, and defines a strut height $h_s$ measured along the longitudinal axis L from the underside 65a of the bottom wall 62 to the distal end surface 122 of the strut 120. When the insert component 14 is positioned within the primary container 12, the distal end surface 122 of the strut 120 abuts/rests against an inner surface of the bottom wall 22 of the primary container 12 to thereby position the main body 60 of the insert component 14 (and the test strips 16 contained therein) at a select height relative to the primary container 12. The insert component 14 is preferably positioned within the primary container 12 at a select height where at least the upper end edges 16a of the test strips 16 are located above the upper surface 25 of the body 20 of the primary container 12 to allow for easy access and grasping of an individual test strip 16 by the user, but with the upper end edges 16a of the test strips 16 positioned below the upper wall 42 of the cap 40 when the cap 40 is in a closed position to prevent bending or damaging of the test strips 16. Although the strut 120 has been illustrated and described as having a substantially rectangular configuration, it should be understood that outer shapes and configurations of the strut 120 are also contemplated.

In the illustrated embodiment, the strut 120 includes a series of break-off or removable tabs or strips 124 that are separated/spaced from one another along the longitudinal axis L by interface regions 126 configured to allow for the selective removal of one or more of the removable tabs 124 from the strut 120. In the illustrated embodiment, the interface regions 126 comprise frangible regions or regions of reduced strength that separate adjacent pairs of the removable tabs 124. The frangible regions 126 define a series of pre-defined fracture initiator zones configured to facilitate initiation of a fracture or break along a select one of the frangible regions 126 upon application of a sufficient torsional or bending force onto the select frangible region so as to allow for removal of a select length of the strut 120 distal of the fracture zone via removal of one or more of the removable tabs 124. The distal-most tab 124 may be provided with a notch or recessed region 128 extending along a portion of the length of the strut 120.

In the illustrated embodiment, the regions of reduced strength defined by the frangible regions 126 are each formed by a localized reduced thickness of the strut 120. In one embodiment, the localized reduced thickness of the frangible regions 126 are provided by grooves or scores extending laterally along opposite sides of the strut 120 in a direction transverse to the longitudinal axis L. However, in other embodiments, the grooves 126 may be defined along a single side of the strut 120. Additionally, although the grooves 126 are illustrated as extending along the entire length dimension of the strut 120, it should be understood that in other embodiments, the grooves 126 may extend along only a portion of the length dimension of the strut 120, or may be intermittently dispersed along the length dimension of the strut 120. It should further be understood that the frangible regions 126 can take on configurations other than grooves, including other structural features that provided a weakened region intermediate adjacent pairs of the removable tabs 124. For example, the frangible regions 126 may comprise localized reductions in the material thickness of the wall of the strut 120 between adjacent pairs of the removable tabs 124, or localized regions of reduced strength intermediate adjacent pairs of the removable tabs 124. In still other embodiments, the interface regions 126 may take on configurations other than the frangible regions. For example, in other embodiments, the interface regions 126 may be configured to allow for the selective removal of one or more of the removable tabs 124 from the strut 120 other than by breaking or fracturing.

As indicated above, one or more of the removable tabs 124 can be removed or broken off at a select one of the frangible regions 126 and removed to thereby change the strut height $h_s$ of the strut 120, which in turn positions the insert component 14 at a lower recessed position within the primary container 12 to accommodate test strips 16 having a greater strip length $l_s$ wherein at least the upper edges 16a of the test strips 16 are located above the upper surface 25 of the body 20 of the primary container 12 to allow for easy access and grasping of an individual test strip 16 by the user. In this manner, the strut height $h_s$ can be selectively and easily adjusted via removal of one or more of the removable tabs 124 to accommodate a wide variety of test strip length $l_s$ while presenting at least the end edges 16a of the test strips 16 at a generally uniform height within the storage container 10 (i.e., at a select distance above the upper surface 25 of the body 20 of the primary container 12) without having to change or reconfigure the primary container 12. As should be appreciated, providing the insert component 14 with a strut 120 having an adjustable strut height $h_s$ provides the storage container 10 with the ability to be used in association with a wide variety of test strip length $l_s$.

In one embodiment, the removable tabs 124 and/or the frangible regions 126 may be configured for releasable engagement with a force application instrument (not shown) to initiate breaking, fracturing or removal of one or more of the strut 120 along a select one of the frangible regions 126. Alternatively, one or more of the removable tabs 124 may be broken off of or otherwise removed from the strut 120 via direct application of a manual force. As should be appreciated, application of a bending or torsional force onto one or more of the removable tabs 124 above a threshold level will cause the strut 120 to fracture or break along a select one of the frangible regions 126, thereby allowing selective separation and removal of a length of the strut 120 distal of the fracture/break zone F. In the illustrated embodiment, the strut 120 includes three of the removable tabs 124. However, it should be understood that the strut 120 may be provided with any number of the removable tabs 124, including one, two, or four or more of the removable tabs 124.

Figure 12:
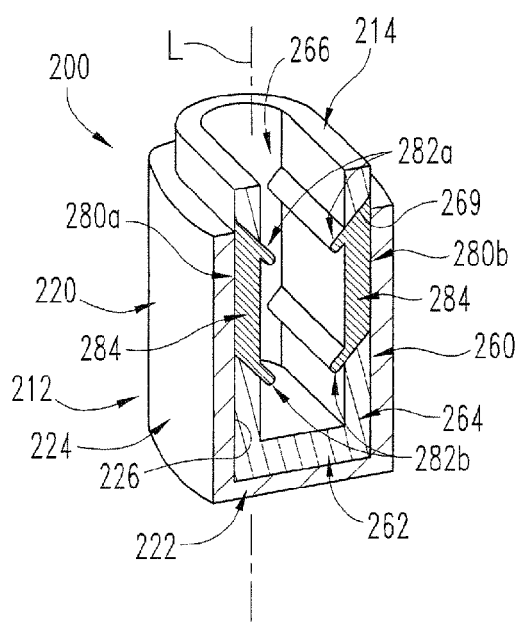
FIG. 12 is a cross sectional perspective view of a storage container for biosensor test elements according to another form of the present invention.

Referring to FIG. 12, shown therein is another form of a storage container 200 for containing and retaining a plurality of vertically oriented articles therein. The storage container 200 extends along a central longitudinal axis L and generally includes a primary container 212 and an insert component 214 positioned within an interior region of the primary container 212 and configured to contain and retain a plurality of vertically oriented articles such as, for example, the biosensor test strips 16 illustrated and described above.

The primary container 212 generally includes a body 220 having a substantially planar bottom wall or base 222, and a tubular sidewall 224 extending axially from the bottom wall 222. The bottom wall 222 and the sidewall 224 together define a cylindrical configuration defining an inner chamber 226 extending generally along a longitudinal axis L. The primary container 212 may include a cap (not shown) removably engagable with the body 220 to close off the storage container 200 to prevent moisture and/or containments from entering the interior region of the storage container 200. In the illustrated embodiment, the body 220 has an oblong form factor defining a generally oval or elliptical-shaped outer cross sectional profile. However, other shapes and cross sections are also contemplated.

The insert component 214 is positioned within the inner chamber 226 of the body 220 of the primary container 212, and is configured to contain and retain a plurality of the biosensor test strips 16 therein. The insert component 214 generally includes a main body 260 having a substantially planar bottom wall or base 262 and a tubular sidewall 264 extending axially from the bottom wall 262. The bottom wall 262 and the sidewall 264 together define a cylindrical configuration defining an interior region 266 extending generally along the longitudinal axis L and sized and configured to receive and maintain the biosensor test elements 16 therein. The main body 260 is provided with a pair of retainer elements 280a, 280b positioned on opposite sides of the tubular sidewall 264 relative to the longitudinal axis L. The retainer elements 280a, 280b in turn define a first pair of retainer tip portion 282a extending laterally into the interior region 266, and a second pair of retainer tip portions 282b extending laterally into the interior region 266 and axially offset from the first pair of retainer tip portions 282a. The first pair of retainer tip portions 282a are positioned adjacent an upper end surface of the sidewall 264 and are arranged in general opposition with one another on opposite sides of the longitudinal axis L, and the second pair of retainer tip portions 282b are positioned adjacent the bottom wall 262 and are arranged in general opposition with one another on opposite sides of the longitudinal axis L. The pair of retainer elements 280a, 280b further include a mounting portion or axial flange 284 configured to interconnect the upper and lower retainer tip portions 282a, 282b with one another. Additionally, the retainer elements 280a, 280b are positioned within corresponding lateral openings 269 extending through opposite sides of the tubular sidewall 264 such that the first and second pairs of retainer tip portions 282a, 282b extend inwardly from inner surfaces of the sidewall 264 and into the interior region 266.

The upper and lower retainer tip portions 282a, 282b defined by the retainer elements 280a, 280b extend into the interior region 266 of the insert 214 at an oblique angle relative to the longitudinal axis L. In one embodiment, the upper and lower retainer tip portions 282a, 282b extend into the interior region 266 at approximately a 135° taper angle relative to the longitudinal axis L. However, other oblique angles are also contemplated. As a result of the shape and configuration of the retainer elements 280a, 280b and the retainer tip portions 282a, 282b, test strips 16 may be loaded into the interior region 266 of the main body 260 via a relatively low strip insertion force to enhance or facilitate loading of the test strips into the storage container 200, while the test strips 16 are retained within the interior region 266 of the main body 260 via a relatively higher removal or retrieval force to prevent accidental spillage and/or unintended or involuntary removal of the test strips 16 from the storage container 200. Additionally, the retainer tip portions 282a, 282b are sized and shaped for resilient deflection during insertion and during removal of the test strips into/out of the interior region 266. Moreover, frictional engagement of the retainer tip portions 282a, 282b with the longitudinal side edges 16c, 16d of the test strips 16 aids in maintaining the test strips 16 in a substantially vertical orientation within the storage container 200 so as to maintain the upper end portions of the test strips in a position that allows for easy access and grasping of an individual test strip by the user to facilitate removal of a selected test strip from the storage container 200.

Figure 13:
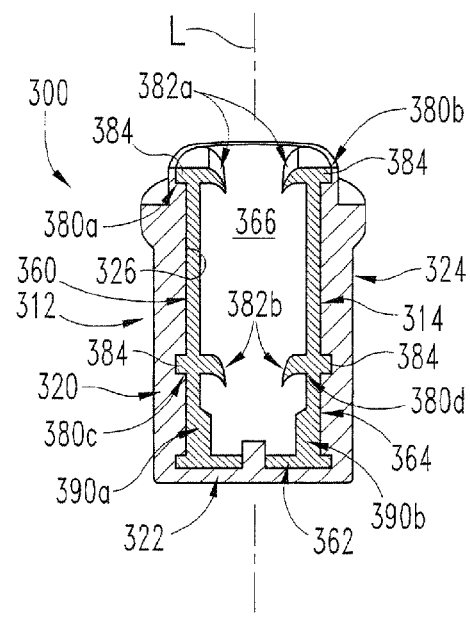
FIG. 13 is a cross sectional perspective view of a storage container for biosensor test elements according to a further form of the present invention.

Referring to FIG. 13, shown therein is yet another form of a storage container 300 for containing and retaining a plurality of vertically oriented articles therein. The storage container 300 generally includes a primary container 312 and an insert component 314 positioned within an interior region of the primary container 312 and configured to contain and retain a plurality of vertically oriented articles such as, for example, the biosensor test strips 16 illustrated and described above.

The primary container 312 generally includes a body 320 having a substantially planar bottom wall or base 322, and a tubular sidewall 324 extending axially from the bottom wall 322. The bottom wall 322 and the sidewall 324 together define a cylindrical configuration defining an inner chamber 326 extending generally along the longitudinal axis L. The primary container 312 may include a cap (not shown) removably engagable with the body 320 to close off the storage container 300 to prevent moisture and/or containments from entering the interior region of the storage container 300. In the illustrated embodiment, the body 320 has an oblong form factor defining a generally oval or elliptical-shaped outer cross sectional profile. However, other shapes and cross sections are also contemplated.

The insert component 314 is positioned within the inner chamber 326 of the body 320 of the primary container 312, and is configured to contain and retain a plurality of the biosensor test strips 16 therein. The insert component 314 generally includes a main body 360 having a substantially planar bottom wall or base 362 and a tubular sidewall 364 extending axially from the bottom wall 362. The bottom wall 362 and the sidewall 364 together define a cylindrical configuration defining an interior region 366 extending generally along the longitudinal axis L and sized and configured to receive and maintain the biosensor test elements 16 therein. The main body 360 is provided with a first pair of retainer elements 380a, 380b positioned on opposite sides of the tubular sidewall 364 adjacent an upper end of the sidewall 364, and a second pair of retainer elements 380c, 380d positioned on opposite sides of the tubular sidewall 364 adjacent the bottom wall 362. The retainer elements 380a-380d in turn define a first pair of retainer tip portion 382a extending laterally into the interior region 366, and a second pair of retainer tip portions 382b extending laterally into the interior region 366 and axially offset from the first pair of retainer tip portions 382a. The first pair of the retainer tip portions 382a are positioned adjacent an upper end surface of the sidewall 364 and are arranged in general opposition with one another on opposite sides of the longitudinal axis L, and the second pair of retainer tip portions 382b are positioned adjacent the bottom wall 362 and are arranged in general opposition with one another on opposite sides of the longitudinal axis L. Each of the retainer elements 380a-380d further includes a mounting portion 384 configured to mount the retainer tip portions 382a, 382b to the tubular sidewall 364.

The upper and lower pairs of the retainer tip portions 382a, 382b extend into the interior region 366 of the insert 314 and include upper and lower surfaces that are each arranged at an oblique angle relative to the longitudinal axis L. In the illustrated embodiment, the upper surface has a convex configuration and the lower surface has a concave configuration, with the upper and lower surfaces intersecting at a relatively pointed distal end. However, other shapes and configurations of the upper and lower surfaces are also contemplated. As a result of the shape and configuration of the retainer elements 380a-380d and the retainer tip portions 382a, 382b, test strips 16 may be loaded into the interior region 366 of the main body 360 via a relatively low strip insertion force to enhance or facilitate loading of the test strips 16 into the storage container 300, while the test strips 16 are retained within the interior region 366 of the main body 360 via a relatively higher removal or retrieval force to prevent accidental spillage and/or unintended or involuntary removal of the test strips 16 from the storage container 300. Additionally, the retainer tip portions 382a, 382b are sized and shaped for resilient deflection during insertion and during removal of the test strips 16 into/out of the interior region 366. Moreover, frictional engagement of the retainer tip portions 382a, 382b with the longitudinal side edges 16c, 16d of the test strips 16 aids in maintaining the test strips 16 in a substantially vertical orientation within the storage container 300 so as to maintain the upper end portions of the test strips 16 in a position that allows for easy access and grasping of an individual test strip by the user to facilitate removal of a selected test strip from the storage container 300.

Additionally, the main body 360 of the insert component 314 is provided with a series of low profile divider elements or lateral projections 390a, 390b extending inwardly from an inner surface of the sidewall 364 and into the interior region 366. The divider elements 390a, 390b are offset from one another along the length dimension of the interior region 366 and also extend along a least a portion of the overall height dimension of the interior region 366. The divider elements 390a, 390b are configured for engagement with the biosensor test strips 16 to aid in maintaining the test strips 16 in a substantially upright orientation within the interior region 366 of the insert component 314 generally parallel with the longitudinal axis L. In the illustrated embodiment, respective pairs of the divider elements 390a, 390b are arranged in opposition to one another across the interior region 366 relative to the longitudinal axis L.

While the invention has been illustrated and described in detail in the drawings and foregoing description, the same is to be considered as illustrative and not restrictive in character, it being understood that only certain embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow.

In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary. As used herein and unless indicated to the contrary, the terms "top" or "upper" refer to portions of the storage container 10 adjacent the cap 40, and the terms "bottom" or "lower" refer to portions of the storage container 10 adjacent the end portion of the storage container 10 opposite the cap 40, and do not necessarily refer to the particular orientation of the storage container 10 when held or manipulated by the user.

What is claimed is:

1. A component for a storage container configured to receive vertically oriented articles, the component comprising:
   a tubular sidewall extending longitudinally from a base, said tubular sidewall comprising an inner surface and an outer surface, said base comprising a support surface and an underside;
   an interior region defined by said inner surface of said tubular sidewall and said support surface of said base, said interior region extending along a longitudinal axis and having a height dimension, a width dimension, and a length dimension;
   at least one spacer portion extending from said underside of said base and configured for engagement with an interior surface of a corresponding storage container;
   at least one pair of retainer elements extending laterally from a portion of said inner surface of said tubular sidewall and inwardly into said interior region, said retainer elements of said at least one pair being oppositely oriented and configured to retain a vertically oriented article therebetween by frictional engagement with opposite longitudinal edges of said article;
   wherein each of said retainer elements comprises a tip portion sized and shaped to engage a corresponding one of said longitudinal edges of said article, said at least one pair of retainer elements sized and shaped for resilient deflection during insertion and during removal of said article therebetween, said retainer elements of said at least one pair being spaced apart sufficiently to removably receive said article therebetween having a nominal width between said opposite longitudinal edges, said retainer elements of said at least one pair being adjustable relative to one another to define a variable separation distance or angular orientation therebetween for engagement with a different vertically oriented article defining a different nominal width between opposite longitudinal edges thereof; and
   wherein an insertion force for resilient deflection of said retainer elements during said insertion of said article is less than a removal force for resilient deflection of said retainer elements during said removal of said article; and
   wherein the component comprises an insert removably positioned within an inner chamber of a storage container; and
   wherein said spacer portion extending from said underside of said base has an adjustable height dimension and is positioned in abutment against an adjacent portion of said storage container to position said insert at a select height within said inner chamber of said storage container; and
   wherein said spacer portion includes at least one removable tab that is selectively removable from a remainder of said spacer portion to vary said adjustable height dimension and correspondingly adjust said select height of said insert within said inner chamber of said storage container.

2. The component of claim 1, wherein said spacer portion includes a plurality of said removable tabs, one or more of said removable tabs being selectively removable from a remainder of said spacer portion to vary said adjustable height dimension and correspondingly adjust said select height of said insert within said inner chamber of said storage container.

3. The component of claim 1, wherein said at least one removable tab is attached to a remainder of said spacer portion by an interface region configured to allow selective removal of said at least one removable tab from said remainder of said spacer portion.

4. The component of claim 3, wherein said interface region comprises a region of reduced strength defining a fracture initiator zone configured to facilitate a fracture along said region of reduced strength to allow for selective removal of said at least one removable tab from said remainder of said spacer portion.

5. The component of claim 4, wherein said spacer portion includes a plurality of said removable tabs, one or more of said removable tabs being selectively removable from said spacer portion along said fracture initiator zone to allow for selective removal of one or more of said plurality of removable tabs to vary said adjustable height dimension and correspondingly adjust said select height of said insert within said inner chamber of said storage container.

6. The component of claim 3, wherein said interface region is defined by a localized reduced thickness of said spacer portion.

7. The component of claim 6, wherein said localized reduced thickness of said spacer portion is defined by one or more grooves extending along a length of said spacer portion.

8. The component of claim 1, wherein said at least one spacer portion comprises a strut extending axially from said underside of said base and defining a strut height defining said adjustable height dimension; and
   wherein said strut has a distal end positioned in abutment against a bottom wall of said storage container to position said insert at said select height within said inner chamber of said storage container.

9. The component of claim 1, further comprising a plurality of raised ribs extending laterally from said outer surface of said tubular sidewall and generally along said longitudinal axis, said plurality of raised ribs configured for retentional engagement with an interior surface of said storage container to retain the component within an inner chamber of said storage container.

* * * * *